United States Patent
Alfano et al.

(10) Patent No.: US 6,615,068 B1
(45) Date of Patent: Sep. 2, 2003

(54) TECHNIQUE FOR EXAMINING BIOLOGICAL MATERIALS USING DIFFUSE REFLECTANCE SPECTROSCOPY AND THE KUBELKA-MUNK FUNCTION

(75) Inventors: Robert R. Alfano, Bronx, NY (US); Yuanlong Yang, New York, NY (US)

(73) Assignee: The Research Foundation of CUNY, New York, NY (US)

( * ) Notice: Subject to any disclaimer, the term of this patent is extended or adjusted under 35 U.S.C. 154(b) by 0 days.

(21) Appl. No.: 09/598,007

(22) Filed: Jun. 19, 2000

Related U.S. Application Data
(60) Provisional application No. 60/177,411, filed on Jan. 20, 2000.

(51) Int. Cl.[7] .................................................. A61B 5/00
(52) U.S. Cl. ................. 600/407; 250/459.1; 250/461.2; 436/63; 436/64; 436/171; 436/172
(58) Field of Search .......................... 600/407, 476–478; 436/63, 64, 171, 172; 250/459.1, 461.1, 461.2

(56) References Cited

U.S. PATENT DOCUMENTS

| | | |
|---|---|---|
| 4,423,736 A | 1/1984 | DeWitt et al. |
| 4,930,516 A | 6/1990 | Alfano et al. |
| 5,261,410 A | 11/1993 | Alfano et al. |
| 5,303,026 A | 4/1994 | Strobl et al. |
| 5,369,496 A | 11/1994 | Alfano et al. |
| 5,645,061 A * | 7/1997 | Kessler et al. .............. 128/897 |
| 5,725,480 A * | 3/1998 | Oosta et al. ................ 600/310 |
| 6,080,584 A * | 6/2000 | Alfano et al. ........... 422/82.08 |
| 6,230,034 B1 * | 5/2001 | Messerschmidt et al. ... 600/322 |

* cited by examiner

Primary Examiner—Ruth S. Smith
(74) Attorney, Agent, or Firm—Kriegsman & Kriegsman (57) ABSTRACT

Method and apparatus for examining biological materials using diffuse reflectance spectroscopy and the Kubelka-Munk function. In one aspect, the method is used to determine whether a tissue sample is cancerous or not and comprises the steps of (a) measuring the diffuse reflectance from the tissue sample at a first wavelength and at a second wavelength, wherein the first wavelength is a wavelength selected from the group consisting of 255–265 nm and wherein the second wavelength is a wavelength selected from the group consisting of 275–285 nm; (b) using the Kubelka-Munk function to transform the diffuse reflectance measurement obtained at the first and second wavelengths; and (c) comparing a ratio or a difference of the transformed Kubelka-Munk measurements at the first and second wavelengths to appropriate standards determine whether or not the tissue sample is cancerous. One can use the spectral profile of KMF between 250 nm to 300 nm to determine whether or not the tissue sample is cancerous or precancerous. According to the value at the first and second wavelengths determine whether or not the malignant tissue is invasive or mixed invasive and in situ or carcinoma in situ.

15 Claims, 11 Drawing Sheets

TECHNIQUE FOR EXAMINING BIOLOGICAL MATERIALS USING DIFFUSE REFLECTANCE SPECTROSCOPY AND THE KUBELKA-MUNK FUNCTION

CROSS-REFERENCE TO RELATED APPLICATIONS

The present application claims the benefit under 35 U.S.C. § 119(e) of U.S. Provisional Patent Application Serial No. 60/177,411, filed Jan. 20, 2000, the disclosure of which is incorporated herein by reference.

STATEMENT REGARDING FEDERALLY SPONSORED RESEARCH OR DEVELOPMENT

This invention was made with Government support under Contract No. DEFG0298ER62560 awarded by the Department of Energy. The Government may have certain rights in this invention.

BACKGROUND OF THE INVENTION

The present invention relates generally to the examination of biological materials using optical spectroscopy and relates more particularly to a novel technique for examining biological materials using diffuse reflectance spectroscopy and the Kubelka-Munk function.

Optical spectroscopy has received increasing attention over the past several years as a tool for use in examining tissues and other biological materials. One such application of optical spectroscopy to the examination of tissues has been in the detection of cancer and precancerous states and has involved the use of native fluorescence spectroscopy. For example, in U.S. Pat. No. 4,930,516 inventors Alfano et al., which issued Jun. 5, 1990, and which is incorporated herein by reference, there is disclosed a method and apparatus for detecting the presence of cancerous tissue using visible luminescence. According to the aforementioned patent, the tissue to be examined is excited with a beam of monochromatic light that causes the tissue to fluoresce over a spectrum of wavelengths. The monochromatic light disclosed in the patent has a wavelength in the range of 350–500 nm. The intensity at which the excited tissue fluoresces is measured either over a spectrum or at a predetermined number of preselected wavelengths, such as at 531 nm, 522 nm and 633 nm. The patent further teaches that one can then determine the carcinomatoid status of the tissue in question by comparing the detected spectrum, one or more peak wavelengths of the detected spectrum, or a ratio or difference of particular wavelengths from the detected spectrum to standards obtained from known tissues.

Other patents and publications that relate to the use of native fluorescence in the detection of cancer and precancerous states include the following: U.S. Pat. No. 5,348,018, inventors Alfano et al., which issued Sep. 20, 1994; U.S. Pat. No. 5,467,767, inventors Alfano et al., which issued Nov. 21, 1995; U.S. Pat. No. 5,131,398, inventors Alfano et al., which issued Jul. 21, 1992; U.S. Pat. No. 5,042,494, inventor Alfano, issued Aug. 27, 1991; U.S. Pat. No. 5,413,108; inventor Alfano, issued May 9, 1995; U.S. Pat. No. 5,769,081, inventors Alfano et al., issued Jun. 23, 1998; U.S. Pat. No. 5,612,540, inventors Richards-Kortum et al., issued Mar. 18, 1997; U.S. Pat. No. 4,957,114, inventors Zeng et al., issued Sep. 18, 1990; Alfano et al., "Light sheds light on cancer-distinguishing malignant tumor from benign tissue and tumors," *The Bulletin of the New York Academy of Medicine*, 67:143–50 (1991); Yang et al., "Optical Spectroscopy of Benign and Malignant Breast Tissue," *Lasers in the Life Sciences*, 7(2):115-27 (1996); Yang et al., "Fundamental Differences of Excitation Spectrum between Malignant and Benign Breast Tissues," *Photochemistry and Photobiology*, 66(4):518–22 (1997); Yang et al., "Excitation Spectrum of Malignant and Benign Breast Tissues: A Potential Optical Biopsy Approach," *Lasers in the Life Sciences*, 7(4):249–65 (1997); Galeotti et al., "On the Fluorescence of NAD(P)H in Whole-Cell Preparations of Tumours and Normal Tissues," *Eur. J. Biochem.*, 17:485–96 (1970); and Japanese Patent Application No. Sho-57-795, published Jul. 15, 1983, all of which are incorporated herein by reference.

In addition, it should be noted that native fluorescence has also been used to detect a number of other abnormal or disease states unrelated to cancer, such as the detection of caries in teeth (U.S. Pat. No. 4,479,499, inventor Alfano, which issued Oct. 30, 1984, and which is incorporated herein by reference) and the detection of atherosclerotic plaque in arteries (U.S. Pat. No. 4,913,142, inventors Kittrell et al., issued Apr. 3, 1990, and which is incorporated herein by reference).

Still another type of spectroscopic technique that has been used to examine tissues has involved the use of Raman spectroscopy. One such application of Raman spectroscopy to the examination of tissues has been in the detection of cancer and is exemplified by U.S. Pat. No. 5,261,410, inventors Alfano et al., which issued Nov. 16, 1993, and which is incorporated herein by reference. In the aforementioned patent, there is disclosed a method for determining if a tissue is a malignant tumor tissue, a benign tumor tissue, or a normal or benign tissue. The method is based on the discovery that, when irradiated with a beam of infrared monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445 and 1651 cm$^{-1}$ for normal or benign tissue, the presence of three Raman bands at a Raman shift of about 1240, 1445 and 1659 cm$^{-1}$ for benign tumor tissue, and the presence of two Raman bands at a Raman shift of about 1445 and 1651 cm$^{-1}$ for malignant tumor tissue. In addition, it was discovered that for human breast tissue the ratio of intensities of the Raman bands at a Raman shift of about 1445 and 1659 cm$^{-1}$ is about 1.25 for normal or benign tissue, about 0.93 for benign tumor tissue, and about 0.87 for malignant tumor tissue.

In addition, as exemplified by U.S. Pat. No. 5,293,872, inventors Alfano et al., which issued Mar. 15, 1994, and which is incorporated herein by reference, Raman spectroscopy has also been used to distinguish between calcified atherosclerotic tissue and fibrous atherosclerotic tissue or normal cardiovascular tissue.

Still yet another type of spectroscopic technique that has been used to examine tissues has involved the use of diffuse reflectance spectroscopy. An example of the application of diffuse reflectance spectroscopy to the examination of tissues is disclosed in U.S. Pat. No. 4,423,736, inventors DeWitt et al., which issued Jan. 3, 1994, and which is incorporated herein by reference. In the aforementioned patent, there is disclosed a method for evaluating erythema (i.e., the reddening of the skin, for example, by sunburn) utilizing skin reflection measurements, said method involving the use of diffuse reflectance spectra within the range of 400 to 700 nm.

Other patents and publications of interest include U.S. Pat. No. 5,369,496, inventors Alfano et al., which issued Nov. 29, 1994; U.S. Pat. No. 5,303,026, inventors Strobl et al., which issued Apr. 12, 1994; Zhadin et al., "Enhancement of the Fluorescence Cancer Diagnostic Method of Tissues Using Diffuse Reflectance and the Analysis of Oxygenation State," *SPIE Proceeding*, 2697:142–8 (1996); and Bigio et al., "Invited: Elastic scattering spectroscopy for diagnosis of tissue pathologies," *OSA Tops on Biomedical Optical Spectroscopy and Diagnostics* 1996, Vol. 3, pp. 14–19, edited by Eva Sevick-Muraca and David Benaron, all of which are incorporated herein by reference.

SUMMARY OF THE INVENTION

It is an object of the present invention to provide a new technique for examining a biological material, such as a biological tissue or cell.

It is yet another object of the present invention to provide a technique as described above that can be used for either in vivo or in vitro examination of a biological material.

It is still yet another object of the present invention to provide a technique as described above that can be used to distinguish benign tumors, like fibroadenomas, and pre-cancer from malignant tumors.

It is still another object of the present invention to provide a technique as described above that can be used to distinguish invasive carcinoma or mixed invasive and in situ from malignant tumor.

In furtherance of the above objects, as well as other objects described below or apparent from the description below, there is provided herein a method for determining whether a tissue or cell sample is cancerous, precancerous or not, said method comprising the steps of: (a) measuring the diffuse reflectance from the tissue or cell sample at at least a first wavelength and a second wavelength, wherein said first wavelength is a wavelength selected from the group consisting of 255–265 nm and wherein said second wavelength is a wavelength selected from the group consisting of 275–285 nm; (b) using the Kubelka-Munk function to transform the diffuse reflectance measurement obtained at said first and second wavelengths; and (c) using said transformed Kubelka-Munk measurement at said first and second wavelengths to determine whether or not the tissue or cell sample is cancerous.

According to another aspect of the invention, there is provided herein a method for examining a tissue or cell sample, said method comprising the steps of (a) obtaining a diffuse reflectance spectrum for the tissue or cell sample over a spectral range of approximately 250 to 650 nm, preferably approximately: 250 to 300 nm; (b) transforming said diffuse reflectance spectrum using the Kubelka-Munk function; and (c) using the transformed Kubelka-Munk function from diffuse reflectance spectrum to determine the levels of constitutents in the tissue or cell sample for which the Kubelka-Munk function is indicative. For example, the transformed Kubelka-Munk function from diffuse reflectance spectrum at about 260 nm, at about 280 nm and at about 480 nm may be used to determine the levels of DNA, protein and fat, respectively, in the tissue or cell sample for use in separating cancer from benign, normal and fibroadenoma tissue. These tissues include GYN, breast, GI, colon and cervix.

It is even yet another object of the present invention to provide a new apparatus for examining a tissue or cell in accordance with the above method.

Additional objects, as well as features, advantages and aspects of the present invention, will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate a preferred embodiment of the invention and, together with the description, serve to explain the principles of the invention. In the drawings wherein like reference letters and numerals represent like parts:

FIGS. 2($a$) through 2($c$) are images of a tissue sample slide containing an invasive ductal carcinoma, a slide containing a 40× enlargement of a malignant portion of said tissue sample, and a slide containing a 40× enlargement of a normal portion of said tissue sample, respectively;

FIGS. 3($a$) and 3($b$) are images of a tissue sample slide containing a fibroadenoma and a 40× enlargement of a portion thereof, respectively;

FIGS. 6($a$) and 6($b$) are graphic depictions of the diffuse reflectance spectra and the KM spectra, respectively, for representative malignant, benign and fibroadenoma tissue samples;

DETAILED DESCRIPTION OF PREFERRED EMBODIMENTS

Because tissues and like biological materials are highly scattering with respect to light, the direct measurement of the absorption spectra of such materials is not easily performed. The Kubelka-Munk function (see e.g., Kubelka et al., "Ein beitrag zur optik der farbanstriche," *Z. Tech. Phys.*, 12:593 (1931); Wesley et al., "Reflectance Spectroscopy," pp. 55–65, Interscience Publishers (1966); and Kubleka, "New contribution to the optics of intensely light-scattering materials. Part I," *J. of the Opt. Soc. Am.*, 38(5):448–57 (1948), all of which are incorporated herein by reference), which is given as $$f \equiv (1-R_\infty)^2/2R_\infty = k/s$$

wherein R is the measured reflectance and k and s are the absorption and scattering coefficients, respectively, of the sample being examined, provides a basis for interrelating measurable reflectance from a sample to the absorption and scattering characteristics of the sample.

The present invention is based, in part, on the unexpected discovery that malignant breast tumor tissue, fibroadenoma (a benign breast tumor comprising epithelial and stromal elements) tissue, and benign breast tissue can be distinguished using the averaged amplitudes of the Kubelka-Munk function (KMF) transform of diffuse reflectance measurements obtained at 255–265 nm and at 275–285 nm. Without being limited to any particular theory as to how the invention operates, the present inventors believe (i), that the respective KMF transform readings at about 280 nm are indicative of the corresponding levels of proteins present in the tissues being examined, (ii) that the respective KMF transform readings at about 260 nm are indicative of the corresponding levels of nucleic acids (such as DNA and RNA) present in the tissues being examined, and (iii) that malignant tissues differ from fibroadenoma and normal tissue with respect to the quantities of proteins and/or nucleic acids (such as DNA and RNA) present therein.

The present invention is also based, in part, of the unexpected discovery that the KMF transform of diffuse reflectance measurements obtained at 480 nm is distinguishable for adipose (i.e., fat) breast tissue and normal breast tissue. Without being limited to any particular theory as to how the invention operates, the present inventors believe that the aforementioned difference at 480 nm is attributable to different levels of β-carotene in adipose and normal tissues.

Additional KMF peaks that were detected by the present inventors are at 420 nm and at 550 nm and are believed to be attributable to the presence of the Soret band of hemoglobin and the Q-band of hemoglobin, respectively, in the tissues being tested.

Consequently, in accordance with the teachings of the present invention, there is disclosed a method for examining a tissue sample, said method comprising the steps of (a) obtaining a diffuse reflectance spectrum for the tissue sample over a spectral range of approximately 250 to 650 nm; (b) transforming said diffuse reflectance spectrum using the Kubelka-Munk function; and (c) using the transformed Kubelka-Munk diffuse reflectance spectrum to determine the levels of constituents in the tissue sample for which the transformed diffuse reflectance spectrum is indicative.

To demonstrate the foregoing method, the measurement of the diffuse reflectance spectra R(λ) from 250 nm to 650 nm for various samples was performed using an automated dual lamp-based spectrophotometer (Mediscience Technology Corp. CD scanner, Cherry Hill, N.J.) in the synchronize scan mode, in which the emission and excitation monochromators were made to scan synchronously on the same wavelengths. Because the diffuse reflectance signal R(λ) depends not only on the absorption and scattering coefficients of the specimen but also on the dispersion and absorption properties of the instrument, which vary with wavelength, a white scatter standard material with no absorption (k=0) in the spectral region of interest was first tested to provide a standard. A truly optimal standardization material would result in $R_{\infty STD}=1$. In the present test experiments, the standard scatter material used was certified Spectralon™ 99% Reflection Standard (Labsphere, North Sutton, N.H.). Under this condition, the ratio $R_{\infty sample}/R_{\infty STD}=r_\infty$ was determined. Accordingly, $r_\infty$ was used to calculate $f(r_\infty)$, the ratio k/s, as follows: $f(r_\infty)=(1-r_\infty)^2/2r_\infty=k/s$. Assuming that $R_{\infty STD}=1$, taking the logarithm of the K-M function yielded log $f(r_\infty)=$log k–log s. Plotting log $f(r_\infty)$ against the wavelength for a particular sample, the resultant curve corresponded to the absorption spectrum of the sample with intercept displacement given by –log s in the ordinate axis. The 's' variation is small in comparison to 'k.'

Excised benign, adipose and malignant breast tissue samples were obtained from St. Vincent Hospital, Memorial Sloan-Kettering Cancer Center, and National Disease Research Interchange (NDRI). The pathology classifications for the various specimens are given below in TABLE I.

TABLE I

| No. | Description | Total |
| --- | --- | --- |
| Malignant | | |
| 1 | Ductal carcinoma | 35 |
| 2 | Lobular carcinoma | 2 |
| 3 | Mixed ductal and lobular carcinoma | 3 |
| 4 | Mucinous carcinoma | 1 |
| Benign | | |
| 5 | Fibrocystic change | 13 |
| 6 | Benign and native tissue | 26 |
| Fibroadenoma | Fibroadenoma | 14 |
| Adipose | | |
| 7 | Adipose | 30 |

Figure 1:
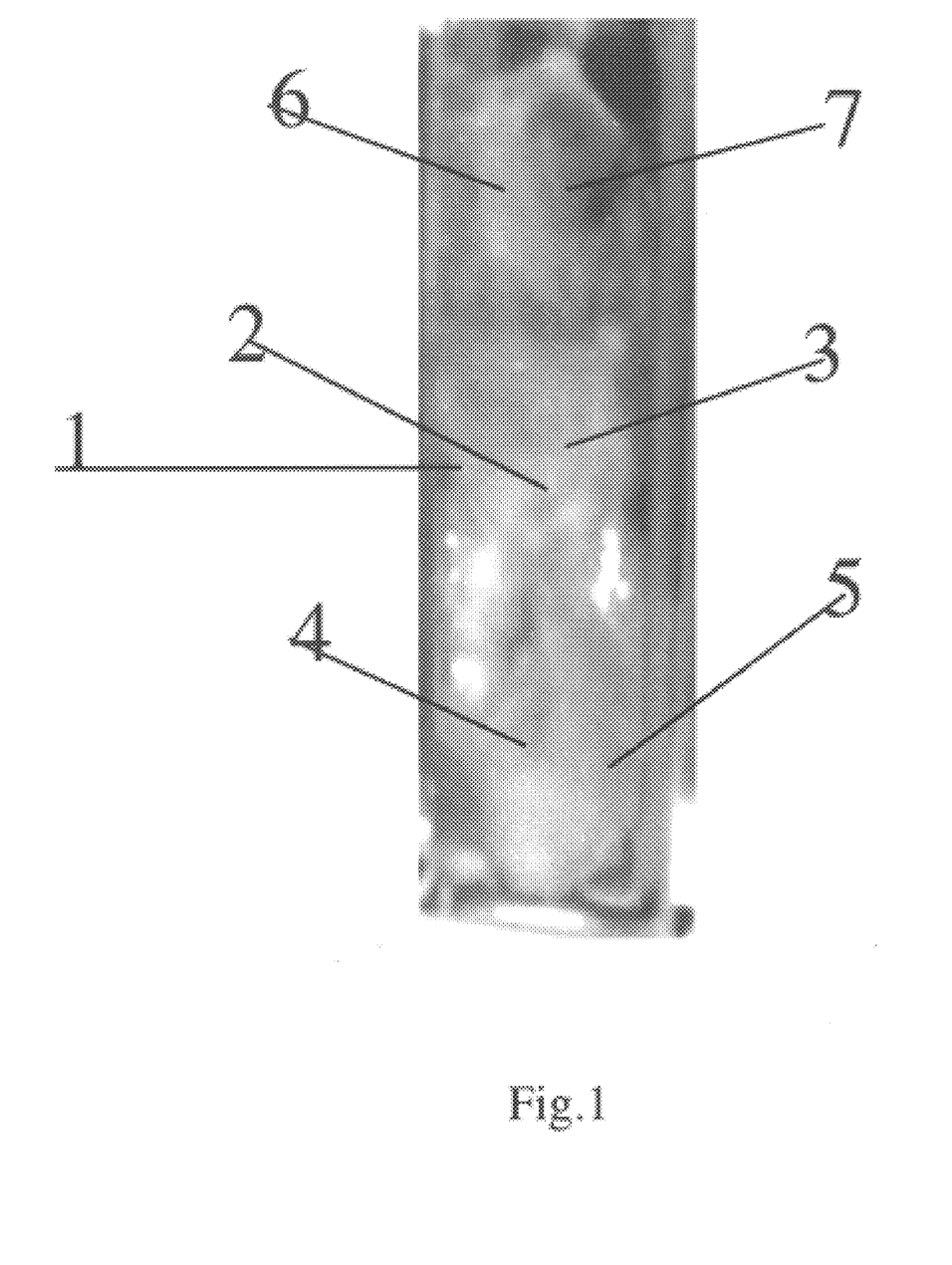
FIG. 1 is an image of a tissue sample in a cuvette prepared for examination by the method of the present invention, the sample having been characterized in a pathological report from Memorial Sloan-Kettering Cancer Center as poorly differentiated carcinoma of breast with historical grade III/III and nuclear grade III/III.

The specimens were neither chemically treated nor frozen prior to spectroscopic measurements. Samples of random shapes obtained from the aforementioned specimens were mounted in a quartz cuvette and closely attached to its inner surface for measurement of spectra. FIG. 1 shows one such sample that was tested using the present method, and certain portions of the sample of FIG. 1 are shown labeled with reference numerals to denote tumor (1–2, 4 and 6–7), benign (3) and fat (5) regions thereof. Diffuse reflectance measurements of the aforementioned regions of the sample of FIG. 1 were taken at various wavelengths, and the results are shown in TABLE II.

TABLE II

| Location | 1 tumor | 2 tumor | 3 benign | 4 tumor | 5 fat | 6 tumor | 7 tumor |
| --- | --- | --- | --- | --- | --- | --- | --- |
| $f(r_\infty)_{275-285\,nm}$ | 10.85 | 12.99 | 2.04 | 14.18 | 15.27 | 3.51 | 12.26 |
| $f(r_\infty)_{255-265\,nm}$ | 14.07 | 30.51 | 1.64 | 31.40 | 38.14 | 3.61 | 13.62 |
| $f(r_\infty)_{480\,nm}$ | 0.03 | 0.04 | 0.12 | 0.06 | 0.41 | 0.10 | 0.06 |

Figure 2A:
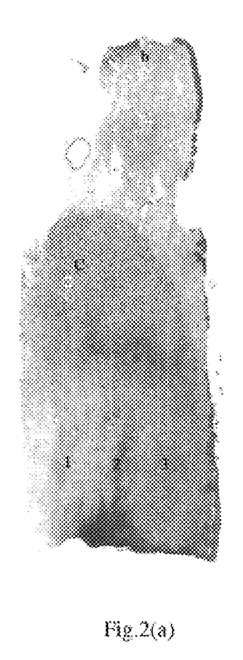
Figure 2B:
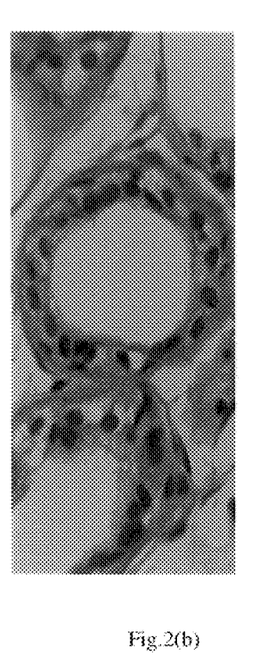
Figure 2C:
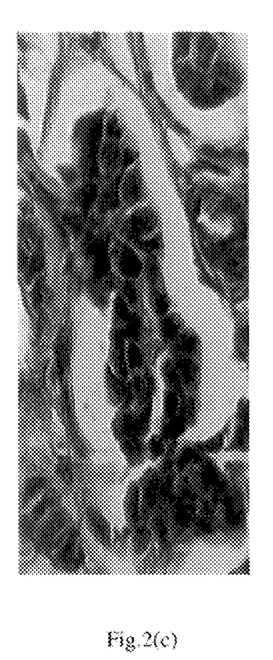
Figure 5:
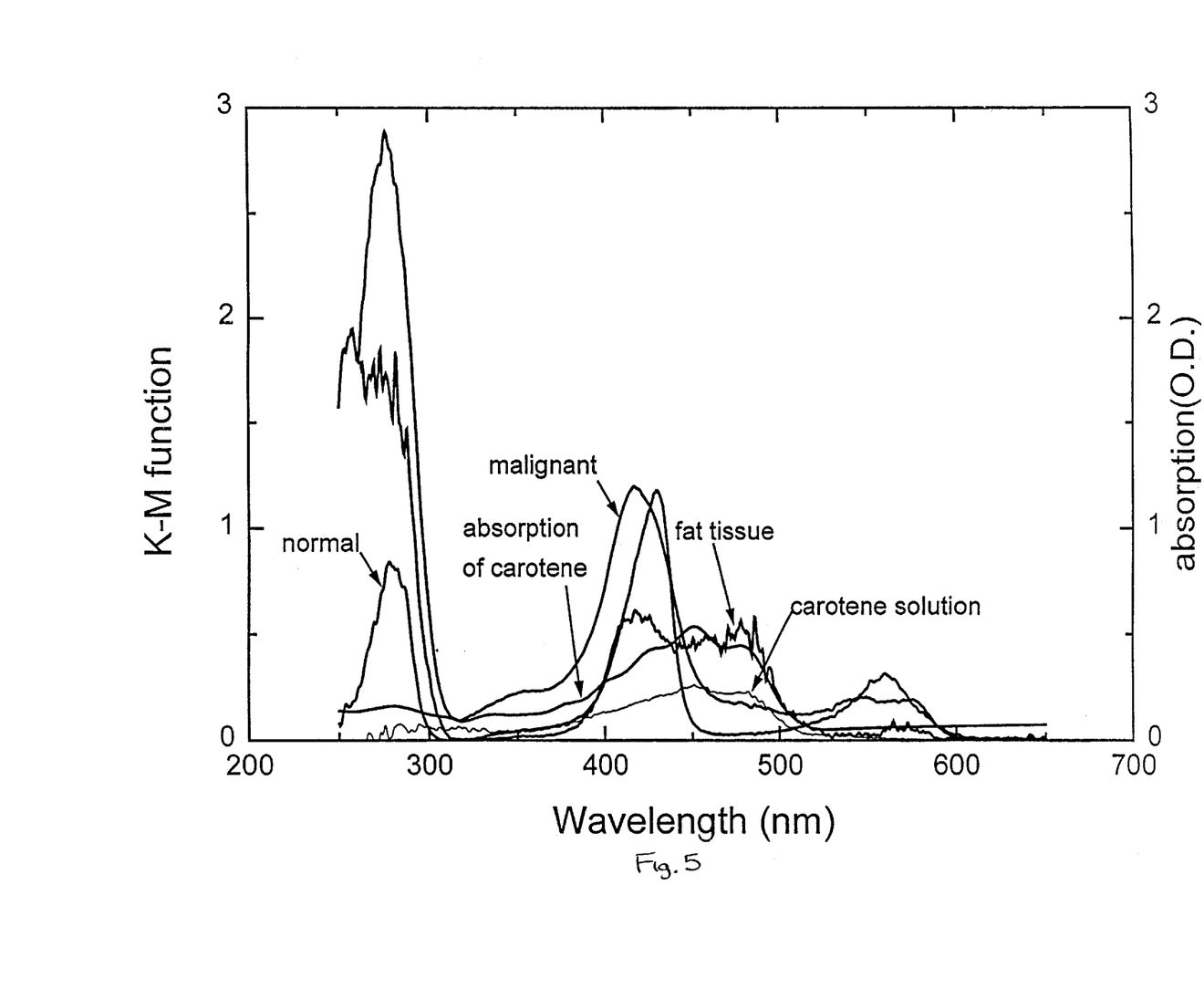
FIG. 5 is a graphic depiction of the Kubelka-Munk function from 250 nm to 650 nm transforms for the spectra of FIG. 4.

Referring now to FIGS. 2(*a*) through 2(*c*), there are shown photographs of a tissue sample slide containing an invasive ductal carcinoma (FIG. 2(*a*)), a slide containing a 40× enlargement of a malignant portion of said tissue sample (FIG. 2(*b*)), and a slide containing a 40× enlargement of a normal portion of said tissue sample (FIG. 2(c)). Diffuse reflectance measurements of those portions denoted areas 1, 2 and 3 in FIG. 2(a) were taken at various wavelengths, and the results are shown in TABLE III.

malignant tissue samples, but there is a definite peak in the KM spectra for the adipose tissue. This result is reflected in the averaged amplitudes of KM function at 480 nm for various tissue types, which are shown in TABLE V.

TABLE V

|  | Invasive Carcinoma | Mixed (in situ and invasive) | Benign | Fibro-adenoma | Adipose |
|---|---|---|---|---|---|
| $f(r_\infty)_{480\ nm}$ | 0.22 ± 0.27 | 0.14 ± 0.10 | 0.12 ± 0.11 | 0.12 ± 0.09 | 0.87 ± 0.39 |

As can be seen, only adipose tissue gives a comparatively high amplitude reading at 480 nm (0.87±0.39).

Figure 6A:
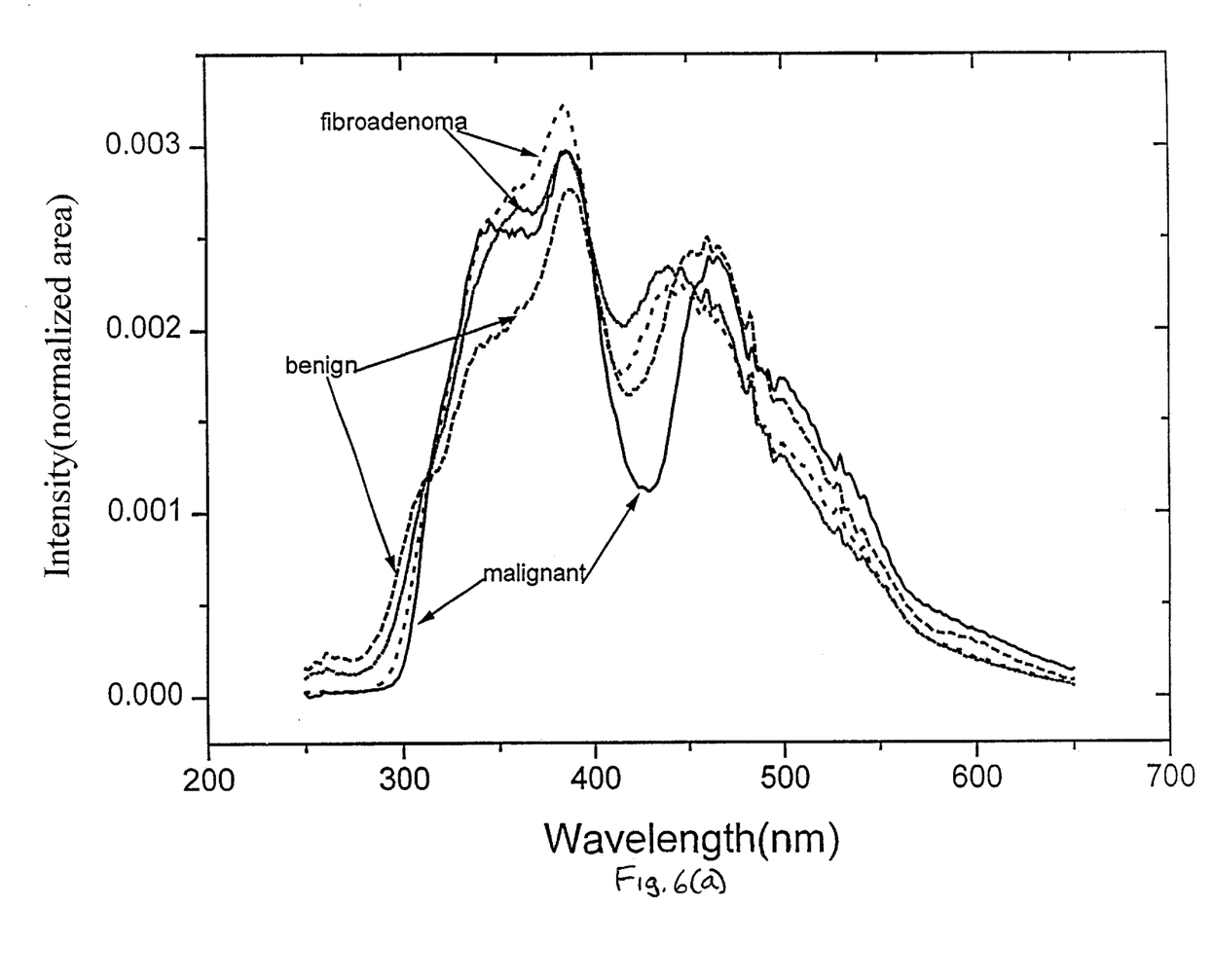
Figure 6B:
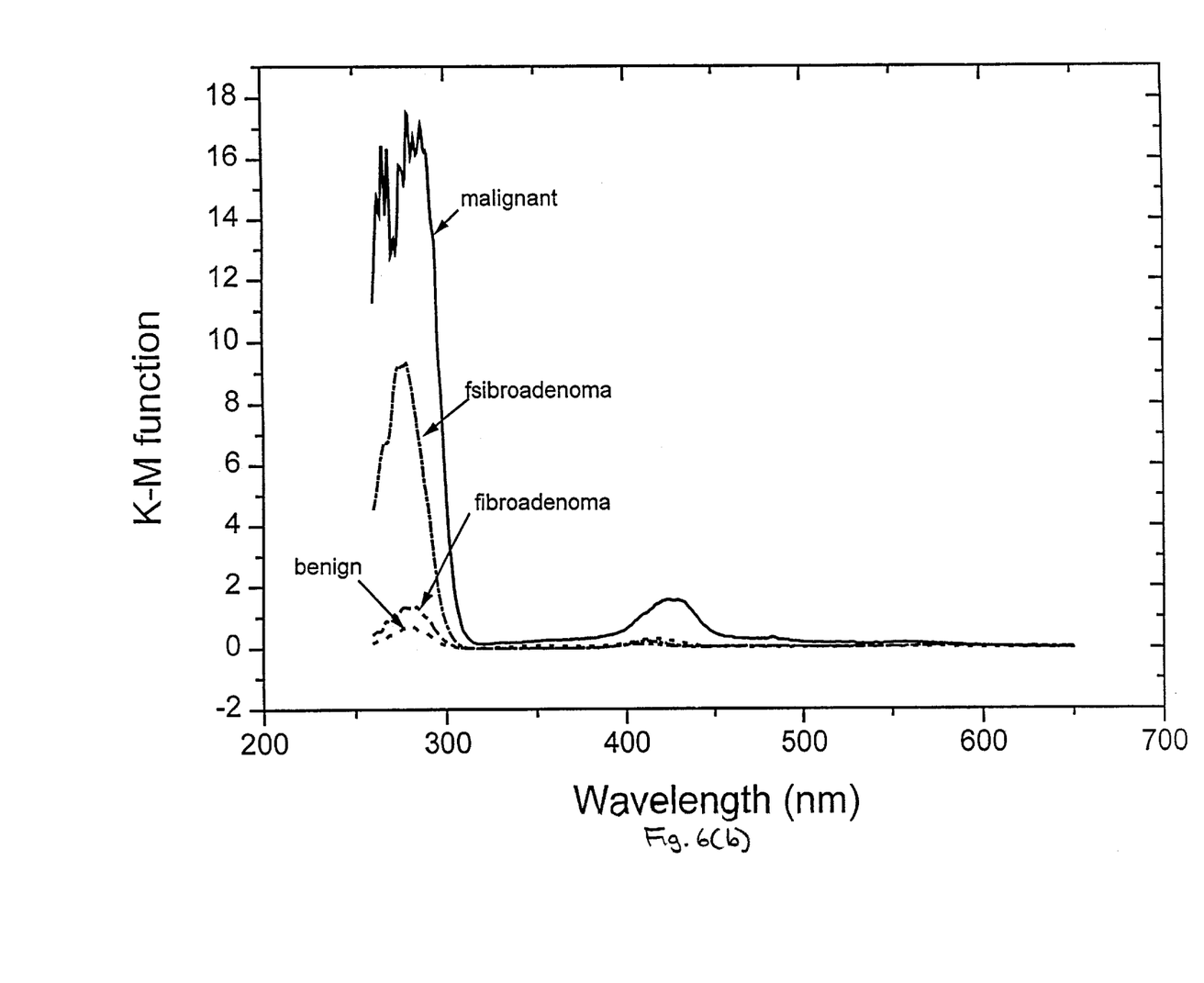

FIGS. 6(a) and 6(b) depict the diffuse reflectance spectra and the KM spectra, respectively, for representative malignant, benign and fibroadenoma tissue samples. As seen in FIG. 6(b), a peak near 280 nm is apparent in the spectra for all tissues, but the amplitude varies for each tissue. In particular, the amplitude for the malignant tissue at 280 nm is higher than for the fibroadenoma and benign tissues. It is believed that this peak corresponds to the absorption of proteins in the tissues. Another peak near 265 nm is only apparent for the malignant tissue. It is believed that this peak corresponds to the absorption of DNA in the malignant tissue. (See Anders, "DNA fluorescence at room temperature excited by means of dye laser," *Chemical Physics Letters*, 81:270–2 (1981), the disclosure of which is incorporated herein by reference.)

TABLE III

| Location | 1 | 2 | 3 |
|---|---|---|---|
| $f(r_\infty)_{275-285\ nm}$ | 8.13 | 7.22 | 7.79 |
| $f(r_\infty)_{255-265\ nm}$ | 10.42 | 10.11 | 9.68 |
| $f(r_\infty)_{480\ nm}$ | 0.12 | 0.04 | 0.08 |

Figure 3A:
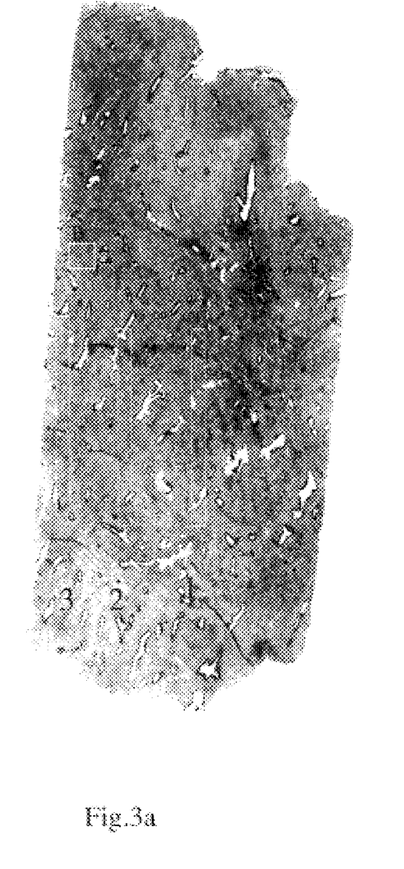
Figure 3B:
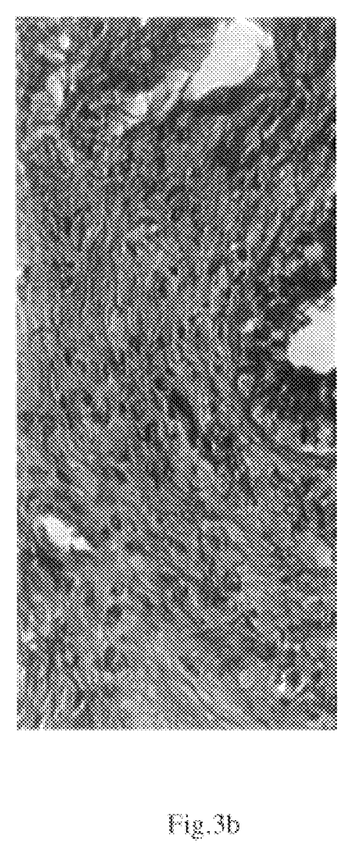

Referring now to FIGS. 3(a) and 3(b), there are shown photographs of a tissue sample slide containing a fibroadenoma (FIG. 3(a)) and a 40× enlargement of a portion thereof (FIG. 3(b)). Diffuse reflectance measurements of those portions denoted areas 1, 2 and 3 in FIG. 3(a) were taken at various wavelengths, and the results are shown in TABLE IV.

TABLE IV

| Location | 1 | 2 | 3 |
|---|---|---|---|
| $f(r_\infty)_{275-285\ nm}$ | 10.68 | 9.90 | 11.12 |
| $f(r_\infty)_{255-265\ nm}$ | 6.19 | 6.11 | 8.25 |
| $f(r_\infty)_{480\ nm}$ | 0.08 | 0.09 | 0.12 |

Figure 4:
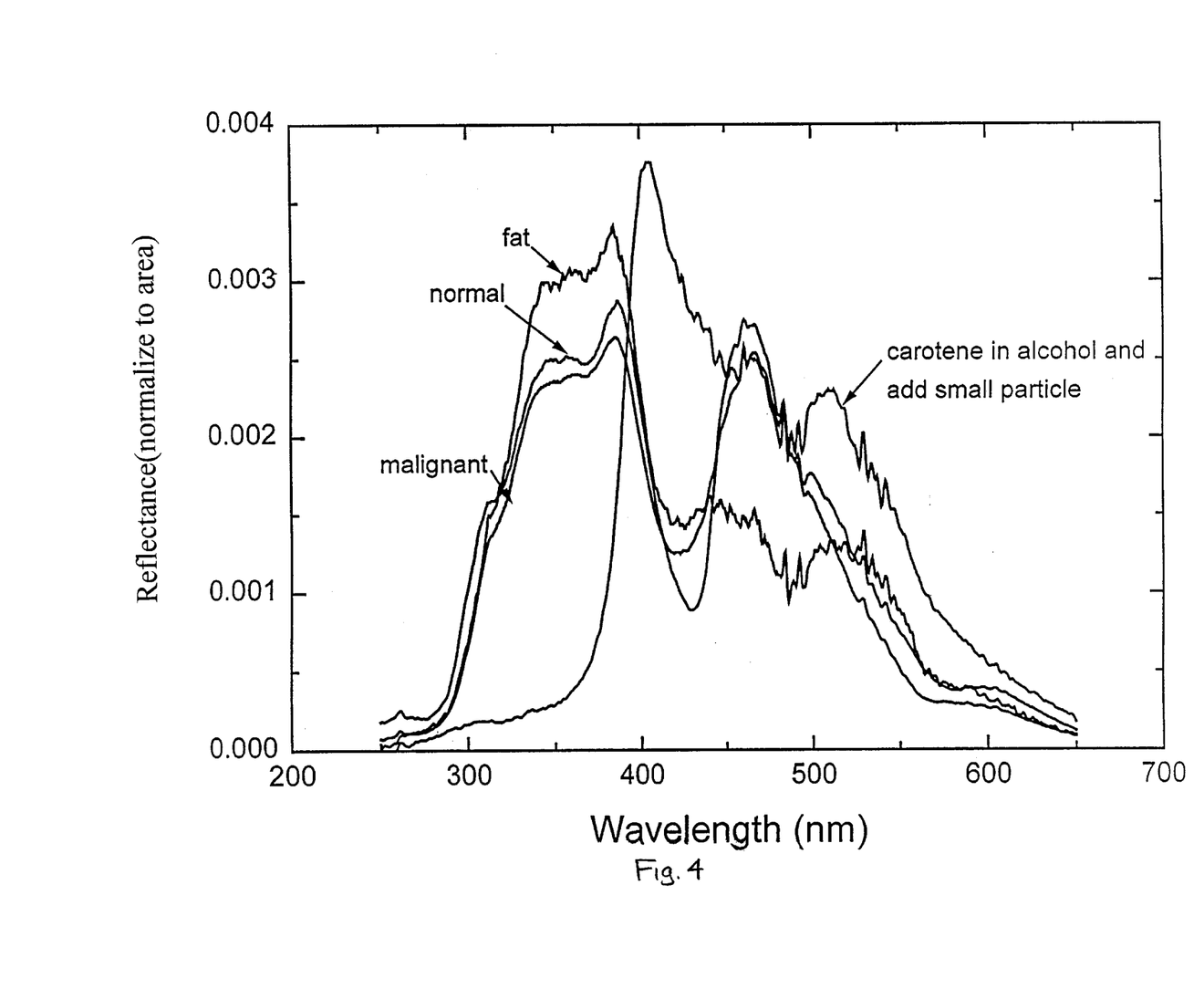
FIG. 4 is a graphic depiction of the diffuse reflectance spectra that were obtained from 250 nm to 650 nm for benign breast, malignant breast and adipose breast tissue samples, as well as for a 0.8 mg/ml β-carotene solution in alcohol.

Referring now to FIG. 4, there are shown the respective diffuse reflectance spectra that were obtained from 250 nm to 650 nm for benign breast, malignant breast and adipose breast tissue samples, as well as for a 0.8 mg/ml β-carotene solution in alcohol. A small particle of $Ti_2O_3$ was added to the β-carotene solution during the diffuse reflectance measurement thereof. The corresponding Kubelka-Munk function transforms for the tissue spectra of FIG. 4 are shown in FIG. 5. As can be seen in FIG. 5, peaks in the KM tissue spectra exist near 265 nm, 280 nm, 420 nm, 480 nm and 550 nm. The absorption spectrum of β-carotene solution is also shown in FIG. 5 for comparative purposes. There is no carotene peak at 480 nm in the KM spectra for the benign or Because there was some fluctuation in the signal in the aforementioned spectral range, the averaged amplitude of KM function from 255 nm to 265 nm and from 275 nm to 285 nm were selected as parameters for use in distinguishing benign, fibroadenoma and malignant (e.g., invasive carcinoma and mixed invasive carcinoma and carcinoma in situ) breast tissues. As noted above, this spectral region, from about 260 nm to 300 nm, is identified with proteins and DNA. The data for KM function, $f(r_\infty)$, and logarithm KM function, $\log f(r_\infty)$, averaged at 255 nm to 265 nm and at 275 nm to 285 nm for various tissues is shown below in TABLE VI.

TABLE VI

| Type of specimen | $f(r_\infty)$ averaged at 275–285 nm | $\log f(r_\infty)$ averaged at 275–285 nm | $f(r_\infty)$ averaged at 255–265 nm | $\log f(r_\infty)$ averaged at 255–265 nm |
|---|---|---|---|---|
| Invasive carcinoma | 13.11 ± 10.39 | 0.98 ± 0.39 | 19.05 ± 18.70 | 1.06 ± 0.52 |
| Mixed invasive and in situ | 5.23 ± 4.16 | 0.58 ± 0.36 | 8.78 ± 13.30 | 0.65 ± 0.50 |
| Benign | 0.88 ± 0.69 | −0.15 ± 0.29 | 0.66 ± 0.70 | −0.36 ± 0.39 |
| Fibroadenoma | 5.23 ± 5.69 | 0.48 ± 0.46 | 3.62 ± 4.41 | 0.24 ± 0.56 |
| Adipose | 4.92 ± 0.69 | 0.50 ± 0.44 | 8.32 ± 10.31 | 0.55 ± 0.68 |

As can be seen from the above data, the values of $f(r_\infty)_{255-265\ nm}$ and $f(r_\infty)_{275-285\ nm}$ are higher for malignant tissues than for benign tissues. For example, with respect to $f(r_\infty)_{275-285\ nm}$, the averaged value is 13.11±10.39 for invasive carcinoma and 0.88±0.69 for benign tissue. The ratio of $f(r_\infty)_{275-285\ nm}$ for invasive tissue to benign tissue is 14.90, and the corresponding ratio for mixed invasive and in situ to benign tissue is 5.94. Differences between the respective values for invasive and benign tissues (i.e., $[f(r_\infty)_{275-285\ nm}]_{invasive} - [f(r_\infty)_{275-285\ nm}]_{benign}$) and between mixed and benign tissues (i.e., $[f(r_\infty)_{275-285\ nm}]_{mixed} - [f(r_\infty)_{275-285\ nm}]_{benign}$) are also distinguishable. However, notwithstanding the fact that the foregoing ratios and differences can be used to differentiate benign and malignant tissues, they cannot as easily be used to differentiate fibroadenoma from malignant tissue. This is because the averaged values of $f(r_\infty)_{255-265\ nm}$ and $f(r_\infty)_{275-285\ nm}$ obtained for fibroadenoma are 3.62±4.41 and 5.23±5.69, respectively, and therefore are considerably higher than the corresponding values for benign tissue.

Figure 7:
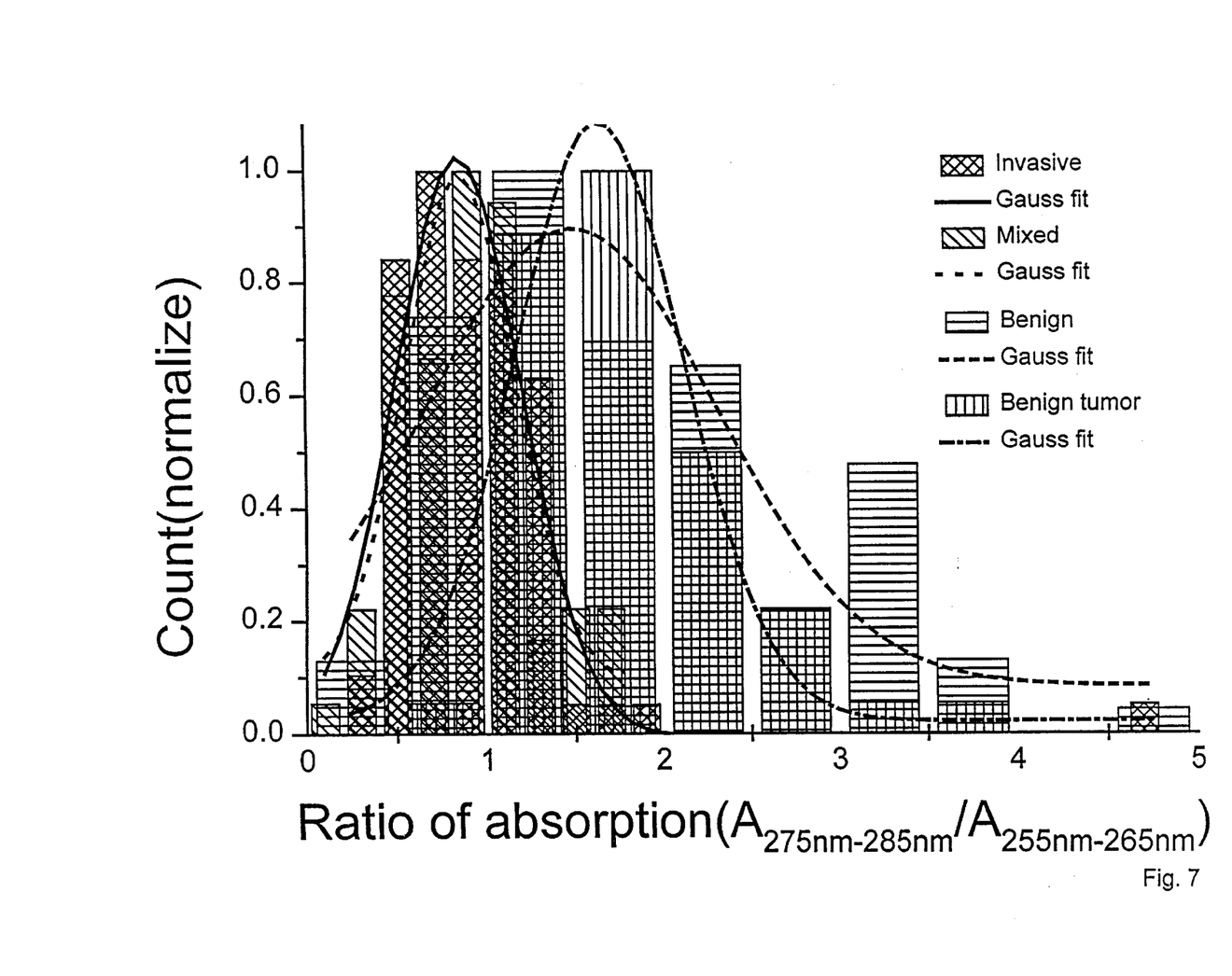
FIG. 7 is a graphic depiction of a histogram of a particular parameter for various tissue states.

Fibroadenoma is the most common neoplasm of the breast; accordingly, it is important that one be able to distinguish fibroadenoma from malignant tissue. As can be seen in TABLE VI, the value for $f(r_\infty)_{255-265\ nm}$ is greater than the value for $f(r_\infty)_{275-285\ nm}$ for malignant tissue whereas the value for $f(r_\infty)_{255-265\ nm}$ is less than the value for $f(r_\infty)_{275-285\ nm}$ for benign and fibroadenoma tissues. Accordingly, the present inventors have devised another ratio parameter $A=[f(r_\infty)_{275-285\ nm}] \div [f(r_\infty)_{255-265}]$ for use in distinguishing fibroadenoma from malignant tissue. Referring now to FIG. 7, there is shown a histogram of parameter A for various tissue states. As can be seen in said histogram, the malignant tissues (i.e., invasive and mixed invasive and in situ) had nearly the same distribution and peak position of a Gaussian fit curve. By comparision, for fibroadenoma and benign tissues, the peak position of the Gaussian fit curve had a larger value than did the corresponding one for the malignant tissue. The statistical averaged values, standard deviations and peak position of Gaussian fit curve of parameter A are given below in TABLE VII.

TABLE VII

| Type of specimen | Statistical mean value and standard deviation for A | Gauss fit center and width for A |
|---|---|---|
| Invasive carcinoma | 0.3 ± 0.52 | 0.85 ± 0.35 |
| Mixed invasive and in situ | 0.89 ± 0.36 | 0.85 ± 0.31 |
| Benign | 1.97 ± 1.42 | 1.49 ± 0.84 |
| Fibroadenoma | 1.82 ± 0.56 | 1.64 ± 0.48 |

To determine whether parameter A has any significance in distinguishing fibroadenoma from malignant tissues, a 't' test was performed. The P value for said test was equal to zero for a group including the invasive carcinoma and fibroadenoma and for a group including the mixed and fibroadenoma. In other words, the difference of parameter A for the different types of tissues was significant.

Figure 8:
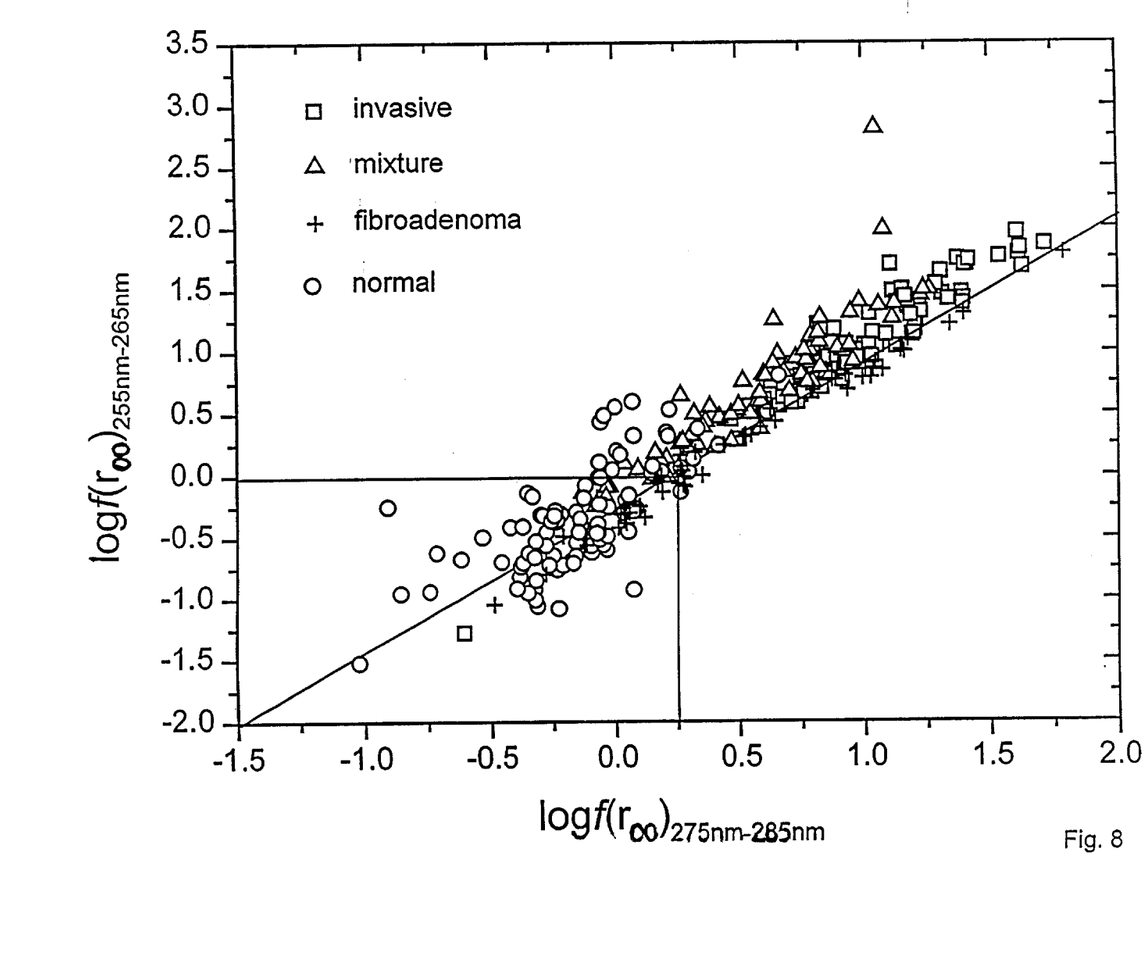
FIG. 8 is a graphic representation of the values for $\log[f(r_\infty)_{275-285\ nm}]$ and $\log[f(r_\infty)_{255-265}]$ plotted along X and Y axes, respectively, for various tissue types.
Figure 9:
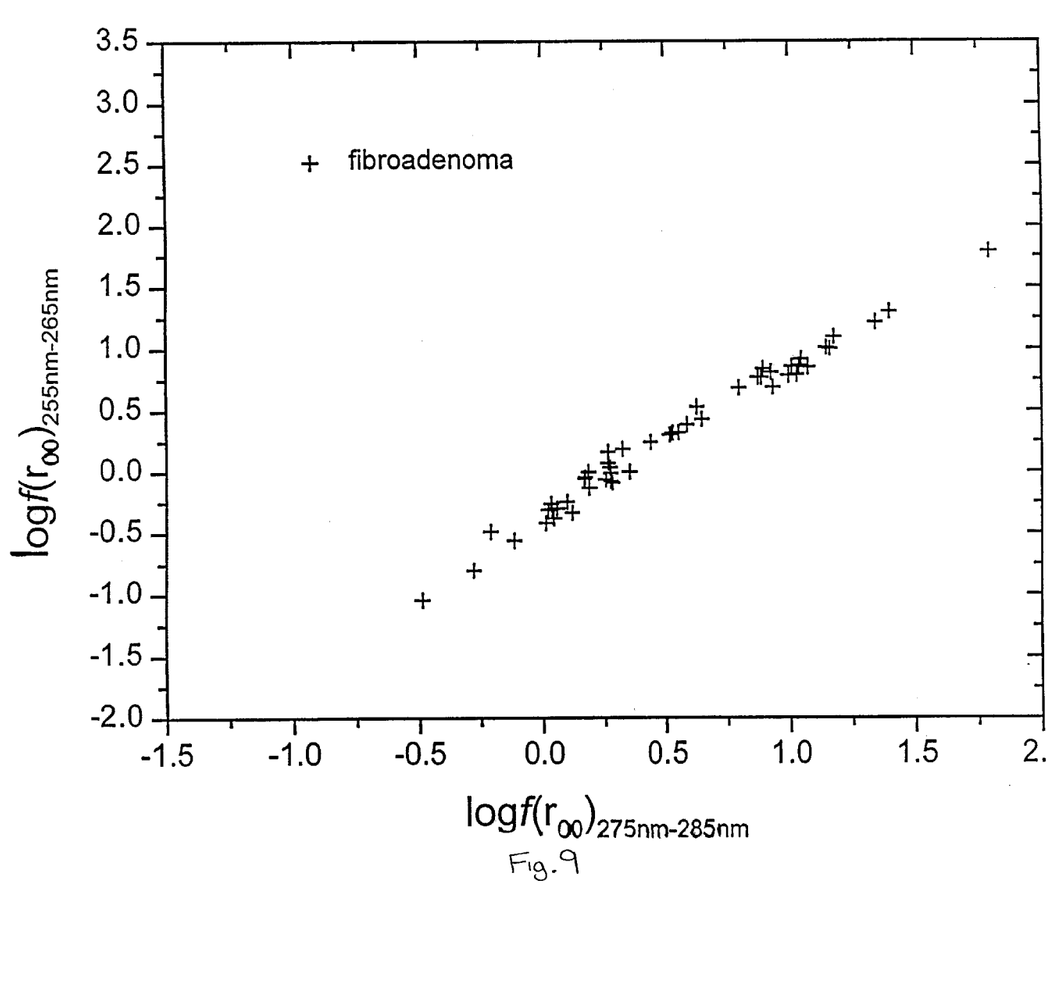
FIG. 9 is a graphic representation of the values for $\log[f(r_\infty)_{275-285\ nm}]$ and $\log[f(r_\infty)_{255-265}]$ plotted along X and Y axes, respectively, for fibroadenoma tissue.

To display these results more clearly, the values for $\log[f(r_\infty)_{275-285\ nm}]$ and $\log[f(r_\infty)_{255-265}]$ are plotted along X and Y axes, respectively, in FIG. 8 for the various tissue types. (Fibroadenoma is shown plotted by itself in FIG. 9.) As can be seen, each tissue type tends to gravitate toward its own zone of this special coordinate system. For benign tissues, the absorption of proteins (275–285 nm) was low, and there was smaller DNA absorption (255–265 nm). For malignant tissues, the protein absorption was relatively high and DNA absorption was detected. For fibroadenoma tissue, the protein absorption was sometimes high, but smaller DNA absorption was detected. By using both the change in DNA and in proteins, malignant tissues can be distinguished from both benign and fibroadenoma tissues. This result makes sense since, when a tissue becomes malignant (especially locally), the DNA content tends to increase.

Figure 10:
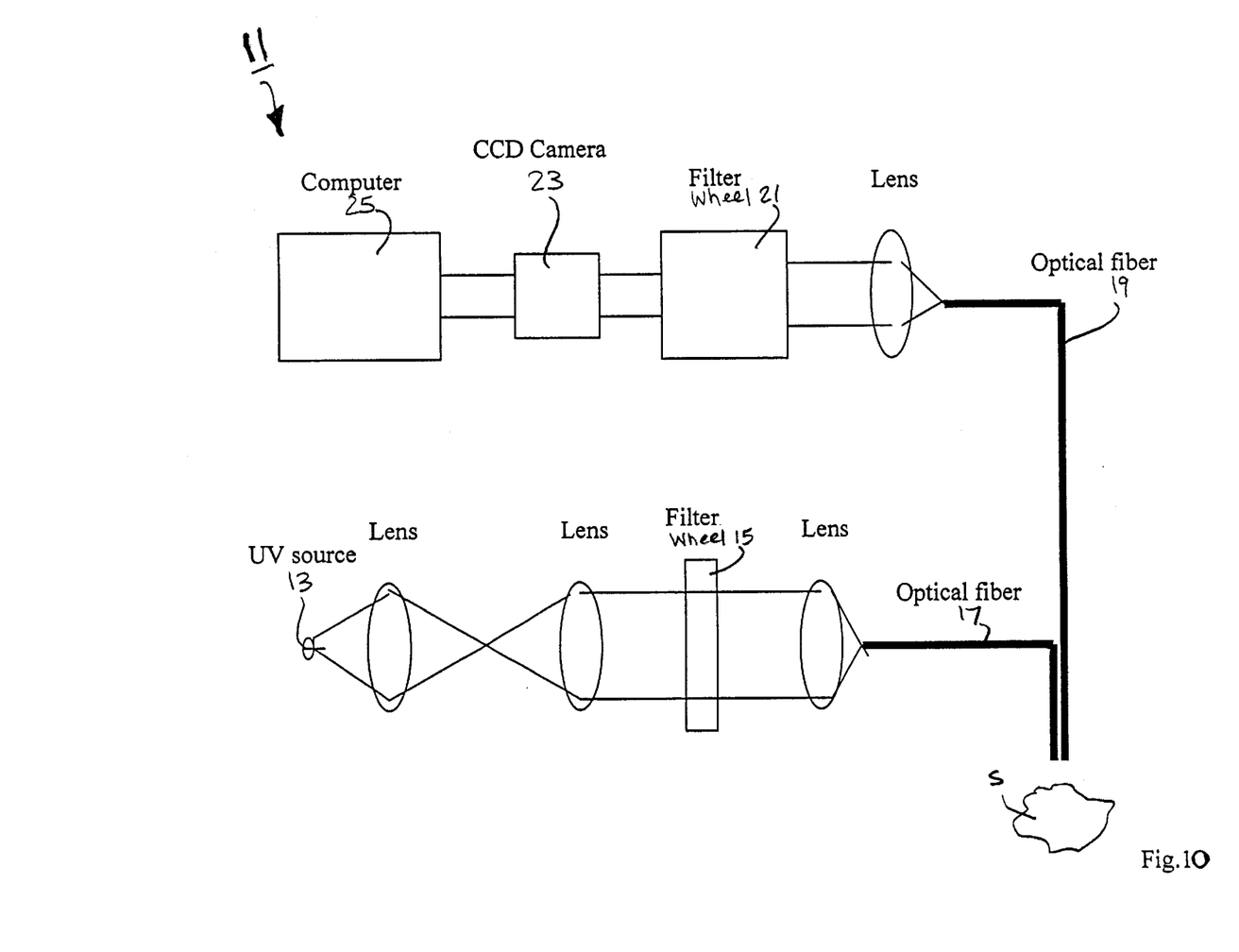
FIG. 10 is a schematic diagram of an experimental setup that may be used to perform the method of the present invention.

Referring now to FIG. 10, there is shown a schematic diagram of an experimental setup that may be used to perform the method of the present invention, said experimental setup being constructed according to the teachings of the present invention and being represented by reference numeral 11.

Setup 11 comprises a UV light source 13 having an adjustable wavelength output, a filter wheel 15 for alternately passing light from UV light source 13 at about 260 nm and at about 280 nm, an optical fiber 17 for illuminating a tissue sample S with said 260 nm or 280 nm UV light passed through wheel 15, an optical fiber 19 for collecting reflected light from the tissue sample S, a filter wheel 21 (or spectrometer) for selectively passing the reflected light at 260 nm and at 280 nm, a CCD camera 23 for detecting the reflected light passed through wheel 21, and a computer 25 for using the Kubelka-Munk function to transform the detected light measurements from CCD camera 23 and for using said transformations to determine the condition of the tissue sample.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for determining whether a cell or tissue sample is cancerous or not, said method comprising the steps of:
    (a) serially illuminating a cell or tissue sample at at least a first wavelength and a second wavelength, wherein said first wavelength is one of a wavelength selected from the group consisting of 255–265 nm and a wavelength selected from the group consisting of 275–285 nm and wherein said second wavelength is the other of a wavelength selected from the group consisting of 255–265 nm and a wavelength selected from the group consisting of 275–285 nm;
    (b) measuring the diffuse reflectance from the cell or tissue sample at at least said first second wavelengths;
    (c) using the Kubelka-Munk function to transform the diffuse reflectance measurements obtained at at least said first and second wavelengths; and
    (d) using the transformed Kubelka-Munk measurements at at least said first and second wavelengths to determine whether or not the cell or tissue sample is cancerous.

2. The method as claimed in claim 1 wherein the cell or tissue sample is selected from a part of the body consisting of the GYN tract, the GI tract, the brain, the kidney, the liver, the cervix, the vagina, the urinary tract, the bladder, the colon and the breast.

3. The method as claimed in claim 1 wherein the cell or tissue sample is a breast tissue sample.

4. The method as claimed in claim 1 wherein the cell or tissue sample is a human breast tissue sample.

5. The method as claimed in claim 1 wherein the cell or tissue sample is an in vivo tissue sample.

6. The method as claimed in claim 1 wherein the cell or tissue sample is an in vitro tissue sample.

7. The method as claimed in claim 1 wherein the cell or tissue sample is a cell sample.

8. The method as claimed in claim 1 wherein said step of using the transformed Kubelka-Munk measurements comprises calculating a ratio of the transformed Kubelka-Munk measurement at said first wavelength and the transformed Kubelka-Munk measurement at said second wavelength and comparing said ratio to appropriate standards.

9. The method as claimed in claim 1 wherein said step of using the transformed Kubelka-Munk measurements comprises calculating a difference of the transformed Kubelka-Munk measurement at said first wavelength and the transformed Kubelka-Munk measurement at said second wavelength and comparing said difference to appropriate standards.

10. The method as claimed in claim 1 said wherein measuring step comprises measuring the diffuse reflectance at only said first and second wavelengths.

11. A method for determining whether a cell or tissue sample is cancerous or not, said method comprising the steps of:
   (a) serially illuminating the cell or tissue sample over the spectral range of about 250 nm to 300 nm;
   (b) obtaining a diffuse reflectance spectrum of the cell or tissue sample over the spectral range of about 250 nm to 300 nm;
   (c) using the Kubelka-Munk function to transform the diffuse reflectance spectrum to obtain a transformed Kubelka-Munk spectrum; and
   (d) comparing the transformed Kubelka-Munk spectrum to appropriate standards to determine whether or not the cell or tissue sample is cancerous.

12. A method for determining whether a cell or tissue sample is cancerous or not, said method comprising the steps of:
   (a) serially illuminating the cell or tissue sample over the spectral range of about 250 nm to 650 nm;
   (b) obtaining a diffuse reflectance spectrum of the cell or tissue sample over the spectral range of about 250 nm to 650 nm;
   (c) using the Kubelka-Munk function to transform the diffuse reflectance spectrum to obtain a transformed Kubelka-Munk spectrum; and
   (d) comparing the transformed Kubelka-Munk spectrum to appropriate standards to determine whether or not the cell or tissue sample is cancerous.

13. The method as claimed in claim 12 wherein the transformed Kubelka-Munk measurements from 250 nm to 650 nm are used to distinguish cancer from normal and precancel in tissues.

14. A method for determining whether a malignant cell or tissue sample is invasive or mixed invasive and in situ or just carcinoma in situ, said method comprising the steps of:
   (a) serially illuminating a malignant cell or tissue sample at at least a first wavelength and a second wavelength, wherein said first wavelength is one of a wavelength selected from the group consisting of 255–265 nm and a wavelength selected from the group consisting of 275–285 nm and wherein said second wavelength is the other of a wavelength selected from the group consisting of 255–265 nm and a wavelength selected from the group consisting of 275–285 nm;
   (b) measuring the diffuse reflectance from the cell or tissue sample at at least said first second wavelengths;
   (c) using the Kubelka-Munk function to transform the diffuse reflectance measurements obtained at at least said first and second wavelengths; and
   (d) using the transformed Kubelka-Munk measurements at at least said first and second wavelengths to determine whether the malignant cell or tissue sample is invasive or mixed invasive and in situ or just carcinoma in situ.

15. An apparatus for determining whether a cell or tissue sample is cancerous or not, said apparatus comprising:
   (a) means for serially illuminating a cell or tissue sample at at least a first wavelength and a second wavelength, wherein said first wavelength is one of a wavelength selected from the group consisting of 255–265 nm and a wavelength selected from the group consisting of 275–285 nm and wherein said second wavelength is the other of a wavelength selected from the group consisting of 255–265 nm and a wavelength selected from the group consisting of 275–285 nm;
   (b) means for measuring the diffuse reflectance from the cell or tissue sample at at least said first and second wavelengths;
   (c) means for transforming the diffuse reflectance measurements obtained at at least said first and second wavelengths using the Kubelka-Munk function; and
   (d) means for determining whether or not the cell or tissue sample is cancerous in accordance with said transformed Kubelka-Munk measurements at at least said first and second wavelengths.

* * * * *